United States Patent [19]

Hussein

[11] Patent Number: 4,768,858
[45] Date of Patent: Sep. 6, 1988

[54] HOLLOW FIBEROPTIC

[75] Inventor: Hany M. G. Hussein, Costa Mesa, Calif.

[73] Assignee: Trimedyne, Inc., Santa Ana, Calif.

[21] Appl. No.: 752,757

[22] Filed: Jul. 8, 1985

[51] Int. Cl.$^4$ .................................................. G02B 6/20
[52] U.S. Cl. .............................. 350/96.32; 350/96.24; 350/96.26; 350/96.33
[58] Field of Search ............... 350/96.24, 96.25, 96.29, 350/96.30, 96.32, 96.33, 96.26

[56] References Cited

U.S. PATENT DOCUMENTS

| | | | |
|---|---|---|---|
| 3,261,356 | 7/1966 | Wallace | 350/96.26 X |
| 3,436,141 | 4/1969 | Comte | 350/96.32 |
| 3,498,286 | 3/1970 | Polanyi et al. | 350/96.26 X |
| 3,583,786 | 6/1971 | Marcatilli | 350/96.32 |
| 4,294,234 | 10/1981 | Matsuo | 350/96.26 X |
| 4,583,539 | 4/1986 | Karlin et al. | 350/96.32 X |
| 4,603,943 | 8/1986 | Okoshi | 350/96.30 |

OTHER PUBLICATIONS

Fiberoptics OISD Encyclopedia 1979, pp. E-97 through E-99.
Presentation No. THAA2, "Self-Imaging by Ring Core Fibers", p. 123, Thomas Niemeier, R. Ulrich, S. B. Poole.

Primary Examiner—John Lee
Attorney, Agent, or Firm—Nilsson, Robbins, Dalgarn, Berliner, Carson & Wurst

[57] ABSTRACT

A fiberoptic includes a guide for light or other electromagnetic energy which has a single fiber core with a ring-shaped cross-section and defines an outer cylindrical surface and an inner cylindrical surface. A cylindrical central hollow channel extends between the ends of the fiberoptic through the center of the single fiber ring-shaped core. Various devices including coherent fiber viewing bundles, hollow tubular transport channels and the like may be slidingly disposed through the center channel of the core.

27 Claims, 1 Drawing Sheet

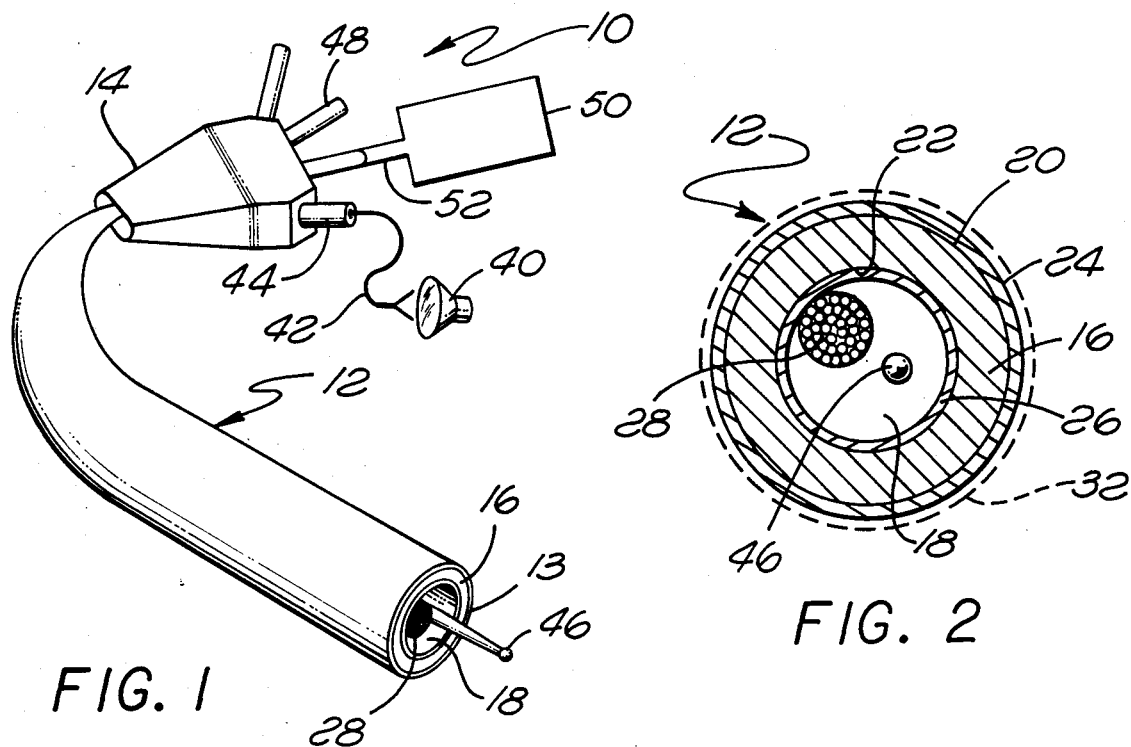
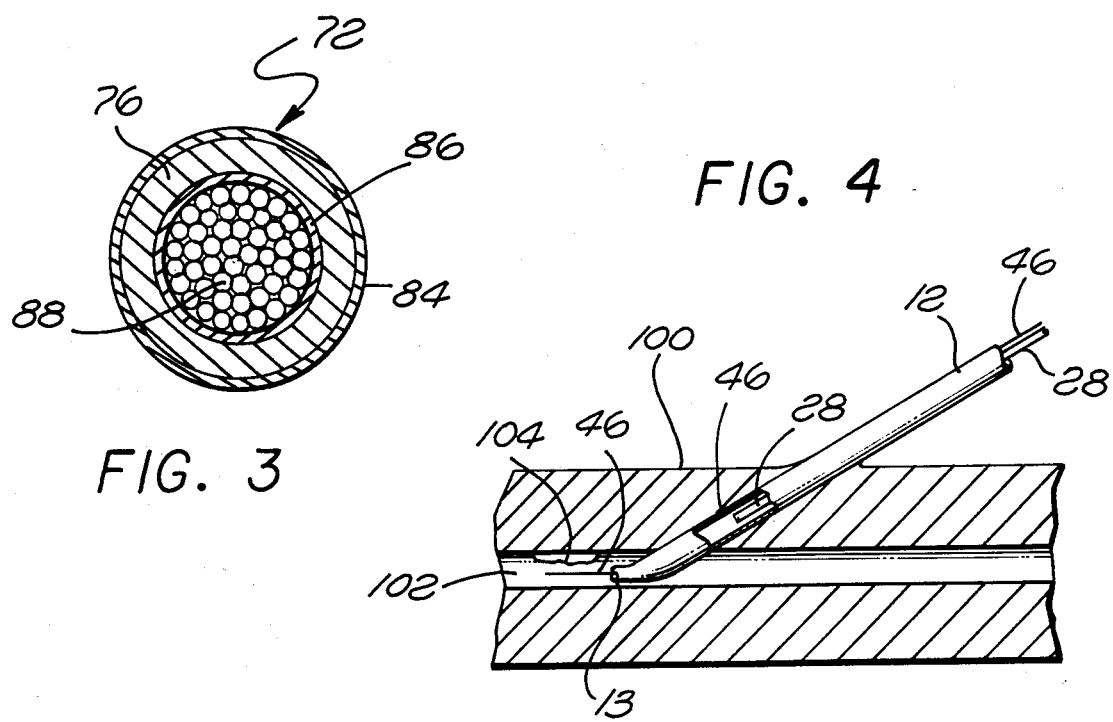

HOLLOW FIBEROPTIC

BACKGROUND OF THE INVENTION

The present invention relates to endoscopic devices and in particular to a fiberoptic having a single fiber light guide which has a ring shaped core with a hollow cylindrical central channel along its length.

The transmission of light through thin fibers of glass or plastics have permitted a variety of instruments for the visualization of otherwise inaccessible organs and tissues inside the human body. Such instruments are broadly referred to as endoscopes and have been useful in the diagnosis and treatment of, for example, gastrointestinal and respiratory diseases.

In recent years, thin, flexible optical fibers have allowed for the remote viewing, photography, biopsy and surgery of organs and tissues. Such thin, flexible optical fibers, also known as fiberoptics, are incorporated in endoscopes to enable the transmission of light to illuminate the internal space being viewed and for enabling the object so illuminated to be viewed. Generally, the viewing capability is accomplished by aligning multiple fibers so that the relative position of each fiber is the same at each end of the bundle. The methods and apparatus for transmitting images therealong is well-known and need not be discussed further.

In addition to light and image transmission, endoscopes frequently have auxiliary channels through which fluids can pass, either from or to the observation site, and by which implements and tools can be remotely controlled. In addition to the above, fiberoptics are used in guiding laser radiation for applications in surgery, fluorescence methods of diagnosis and high intensity illumination. The fiberoptics in endoscopes have also been applied to the development of a variety of transducers for the measurement and monitoring of parameters such as blood flow, temperature, pressure and the like.

Recent developments have involved the use of fiberoptics in an endoscope known as a cardioscope to allow for visualization of intracardial structures. This field, better known as angioscopy, may be defined as the technique for visualization of the inner surfaces of blood vessels by means of the cardioscope. Since its introduction, advances in the use of the cardioscope have enabled the fiberoptics to be inserted into arteries and vessels to enable visualization. A flexible fiberoptic scope has also be recently used to beam laser energy and to observe orifices in the coronary arteries of patients.

Because of these advances in the application of endoscopes, there is a continuing need to develop fiberoptics of very small diameter which are nevertheless capable of performing all of the above described functions. Typical endoscopes presently include a bundle of fiberoptics each having a light transmitting core and an outer cladding. The light enters the end of the core and is reflected by the cladding so as to pass down the core to the other end. A multiplicity of such fiberoptics may be gathered together into a bundle along which light passes to illuminate the object at the distal end of the endoscope. A second bundle, arranged in a coherent manner, may also be incorporated to provide a means of viewing the illuminated area at the distal end of the endoscope. Various other channels may be provided for the transmission of fluids, the control of miniature tools or surgical instruments or any other desired function. The illuminating bundle, the visualizing bundle and the auxiliary channels are gathered together in a multi-lumen or hollow cylindrical sheath. The sheath necessarily has a thickness which increases the thickness and bulkiness of the endoscope, often preventing its use in smaller vessels of the body. Therefore, it is desired to make an endoscope which has a decreased diameter to thereby increase the application of the endoscope in examining increasingly smaller blood vessels and for other uses as well.

Various constructions have been proposed for endoscopes. For example, endoscopes have been developed where the viewing bundle is centrally disposed with the illuminating bundle consisting of a multiplicity of optical fibers surrounding the central viewing bundle so that the viewing bundle and the illuminating bundle are in co-axial alignment. (See "Fiberoptics", *Fiberoptics OISD Encyclo- pedia* 1979 at page E-97 through E-99.) At the recent OFS proceedings in Presentation No. THASS2 entitled "Self-Imaging By Ring Core Fibers", page 123, OFS Thursday, Feb. 18 1985, Niemeier, Ulrich and Poole presented a multi-mode optical wave guide which incorporated a single mode ring core fiber.

However, heretofore there has still been no means of eliminating the sheath of the endoscope. The present invention provides a single optical fiber with a hollow center core through which a viewing bundle, one or more transport channels or any of the other devices used in endoscopes may be positioned and having a ring shaped cross-section around the central channel which ring-shaped section provides a light pathway for illuminating an object at the distal end of the endoscope. The ring-shaped cross-section core has cladding both on the inside and on the outside. Because the core is a single fiber, it can act as both a sheath and light guide allowing the conventional sheath tubing to be eliminated. The result is the reduction of the outer diameter of the elongated viewing portion of the device making it possible to visualize, for example, small blood vessels.

In the preferred embodiment, the hollow fiberoptic is made from plastic and has a hollow center cylindrical region through which a glass or plastic coherent bundle may be slidably received.

In an alternative embodiment, the hollow fiberoptic will be an integral part of the viewing structure. This can be accomplished by filling the preform of the hollow fiberoptic with multiple solid fiberoptics arranged in a coherent manner. When the resulting assembly is drawn through an oven, a structure is generated which contains a plastic coherent bundle surrounded by a single plastic hollow fiberoptic. Such a structure will have favorable physical characteristics with a substantially reduced manufacturing cost.

A particular advantage of the hollow fiberoptic is the existence of the central hollow channel which can be used, for example, to guide the hollow fiberoptic over a flexible guide wire which has been placed across an obstruction of a blood vessel to thereby be able to very precisely position the end of the fiberoptic adjacent a location predefined by a guide wire. Sliding the hollow fiberoptic over this guide wire allows safe guidance of this fiberoptic inside the blood vessel with a minimum risk of vessel perforation. Yet another application of the hollow fiberoptic in accordance with the invention is as a sensor which can again be guided over a guide wire into the vessel of choice. Finally, the central channel of the hollow fiberoptic in accordance with the invention could be used to deliver various solutions and medications into the body while performing diagnostic functions or therapeutic functions such as laser recanalization.

The present invention is particularly useful in performing laser recanalization. This procedure positions a coherent light bundle adjacent an obstruction in a vessel. Laser energy is then directed at the obstruction to vaporize and thereby eliminate the obstruction. A particularly serious problem using present endoscopes and techniques has been the inability to position the laser carrying coherent bundle so that it points at the obstruction and not at the sidewall of the vessel. If the laser is directed toward the vessel wall rather than the obstruction, the laser energy will perforate the vessel wall thereby greatly increasing the risk to the patient. It is therefore desired to provide an endoscope which will more accurately position a laser transporting coherent bundle so that it points at the obstruction rather than in another direction. The present invention substantially solves this positioning problem since the coherent bundle is held about its circumference in position by the single hollow fiberoptic which can be accurately positioned by sliding the single hollow fiberoptic over a flexible guide wire previously placed across the obstruction of the blood vessel.

SUMMARY OF THE INVENTION

A fiberoptic for an endoscope includes a light guide comprised of a single fiberoptic with a ring-shaped cross-section and a central channel, the fiberoptic having an outer cylindrical surface, an inner cylindrical surface and a cylindrical center channel which extends through the center of the fiberoptic along the length thereof to provide a communication channel between opposite ends of the fiberoptic.

Outer cladding is disposed over the outer cylindrical surface of the single fiberoptic and inner cladding is disposed on the inner cylindrical surface of the fiberoptic.

In one embodiment, a coherent bundle of fiberoptics (herein optical fiber viewing bundle) is disposed in the center channel. In another embodiment, a hollow tubular transport channel is also disposed in the center channel whereby substances may be transported between the opposite ends of the fiberoptic through the transport channel. In accordance with yet another embodiment of the invention, the fiberoptic, outer cladding and inner cladding are made of optical grade plastic, quartz or glass or a combination of plastic, quartz or glass. If glass is used, a fourth layer of plastic (over the outer surface) may be used to provide flexibility and integrity of the structure and to protect a patient should the glass of the fiberoptic break.

In one embodiment, a coherent fiber viewing bundle is slidably received in the center channel preferably leaving sufficient space in this channel to allow transport of fluids or other substances, or to allow passage of various devices commonly used with catheters and/or endoscopes. In another embodiment, the hollow fiberoptic incorporates a centrally disposed viewing bundle along the center channel in integral relationship thereto.

A BRIEF DESCRIPTION OF THE DRAWINGS

A complete understanding of the present invention and of the above and other advantages may be gained from a consideration of the following description of the preferred embodiments taken in conjunction with the accompanying drawings in which:

FIG. 1 is a pictorial illustration of an endoscope incorporating a fiberoptic in accordance with the invention;

FIG. 2 is a cross-sectional view of the fiberoptic illustrated in FIG. 1;

FIG. 3 is a cross-section of an alternative embodiment of an endoscope where the fiberoptic incorporates a centrally disposed viewing bundle along the center channel in integral relationship thereto;

FIG. 4 is an illustration of the use of the invention, for example, in laser recanalization.

DETAILED DESCRIPTION

Referring initially to FIG. 1, a representative endoscope device 10 incorporates a fiberoptic 12 which comprises a single fiber hollow center light guide with a distal end 13. The fiberoptic 12 is coupled to a housing 14 which provides access to various parts of the fiberoptic structure 12.

Referring to FIG. 1 in conjunction with FIG. 2, the fiberoptic 12 includes a fiber 16 which comprises a single unitary fiberoptic having a ring-shaped cross-section with a central channel 18 therethrough. The fiber 16 has an outer cylindrical surface 20 and an inner cylindrical surface 22. In the preferred embodiment, an outer cladding 24 is disposed to cover the outer cylindrical surface 20 and an inner cladding 26 is disposed to cover the inner cylindrical surface 22.

In the most basic form of the invention, the central channel 18 is hollow to enable access at the distal end 13 from the housing 14 through the central channel 18.

In operation, illuminating light from an illuminator 40 enters a coupling light guide 42 which is attached to an illuminator port 44 in the housing 14. The housing 14 couples the light guide 42 to the fiber 16 of the fiberoptic 12 so that the light travels from the illuminator 40, through the coupling light guide 42, down the fiber 16 to the distal end 13 of the fiberoptic 12 to illuminate an object. The central channel 18 provides an access channel to the region adjacent the end 13 of the fiberoptic 12.

For example, in FIGS. 1 and 2, a coherent fiber viewing bundle 28 is slidably positioned in the central channel 18 to permit viewing of the region adjacent the remote end 13 of the fiberoptic via a viewing system 50. The space between the inner bundle and interior surface of the central channel 18 could be used to deliver various solutions and medications into the body or provide a means of withdrawing tissue or fluid from inside a patient. The central channel 18 may itself be coupled to a central channel port 48 in the housing 14. The coherent fiber viewing bundle 28 may similarly be coupled to the viewing or laser system 50 via a viewing bundle port 52.

It will be appreciated that various other devices and mechanisms can be inserted through the hollow central channel 18 to provide access to the subject adjacent the end 13 of the fiberoptic 12. In another application, the central channel 18 of the hollow fiberoptic 12 can be used to place the hollow fiberoptic 12 over flexible guide wire 46 which was previously inserted into the body in a subcutaneous manner, to accurately position the guide wire adjacent a selected intravascular structure of a human body. The hollow fiberoptic is then slid over the guide wire thereby allowing safe guidance of the fiberoptic inside the cardiovascular system of the subject with a minimum risk of vessel perforation.

Accordingly, referring to FIG. 4, a fiberoptic system in accordance with the invention may include a flexible guide wire 46 for insertion into the biological subject 100 such as by subcutaneous insertion into the vascular system 102 of the biological subject 100 to a position adjacent a predefined location 104 inside the biological subject 100. The fiberoptic as heretofore described is slidingly positioned over the guide wire 46 and is advanced along the guide wire until the distal end 13 of the fiberoptic is adjacent to the predefined location. At this juncture, the guide wire can either remain in place or may be withdrawn as desired. An optional laser fiber 28, which may be a single fiber or a bundle of coherent fibers, may then be slidingly inserted through the hollow center of the fiberoptic until the distal end of the laser fiberoptic (laser fiber) is adjacent the predefined location. A laser energy source 50, which may be incorporated as part of the system, is then interconnected to either the laser fiber 28 or the hollow fiberoptic itself to provide laser energy through the laser fiber or hollow fiberoptic to the predefined location so that laser energy may be precisely directed at the predefined location 104. It is emphasized that the laser fiber can be eliminated and the hollow fiberoptic itself used to transmit the laser energy to the predefined location 104.

When a coherent bundle (or single optical fiber) 28 is used for laser recanalization, a laser system may be coupled to the coherent optical fiber bundle 28 (or, if desired a separate coherent optical fiber, or the hollow fiberoptic itself without the fiber bundle 28) and laser energy transported through the coherent optical fiber viewing bundle, or the fiberoptic itself, to the distal end 13 of the fiberoptic 12. Because the coherent bundle is in the center of the fiberoptic 12, or alternatively because the fiberoptic itself is used to transmit the laser energy, the laser energy can be precisely positioned and directed at a location adjacent the distal end. Further, the distal end can be accurately and precisely positioned by first sliding the fiberoptic over the guide wire previously positioned ajdacent the desired location.

Additionally, the hollow fiberoptic in accordance with the invention can be utilized to permit sensor access to a region of the subject's body adjacent the end 13 of the fiberoptic 12. Finally, as previously indicated, the central channel 18 of the hollow fiberoptic can be used to deliver various solutions and medications into the body while performing a diagnostic function such as sensing or a therapeutic function such as recanalization.

The fiber 16, outer cladding 24 and inner cladding 26 are preferably made with plastic with selective refractive-indices which confine the light from the illuminator 40 in the fiber or light guide cylinder 16. Hence, light entering the end of the coupling light guide 42 adjacent the illuminator 40 will pass with minimum attentuation along the light guide cylinder 16 and will be delivered from the remote end 13 of the fiberoptic 12.

Typical plastics which form the fiber, inner cladding and outer cladding may include methyl methacrylate; polystyrene for the fiber and lucite (polymethylmethacrylate) for the cladding; or a mixture of polystyrene and polymethyl methacrylate for the claddings.

Because the light cylinder 16 is a single fiber, the necessity for a sheath is eliminated and the fiber 16 itself serves the dual function of being a light guide to transmit illuminating light energy to the remote end 13 of the fiberoptic 12 and a sheath to surround the visualization bundle, and the like which are inserted through the central channel 18. The resultant fiberoptic 12 can therefore be made considerably smaller than fiberoptics requiring a sheath. For example, the diameter of the fiberoptic 12 can be made as small as 0.75 mm or smaller thereby allowing the endoscope 10 to be utilized, particularly in cardiovascular applications, to view a significantly larger number of vessels.

Although as sheath is not necessary, an outer protective jacket 32 may be disposed around the fiberoptic, particularly when the fiberoptic is made of glass, to protect the patient from injury should the fiberoptic break during use.

Referring to FIG. 3, another embodiment of the single fiber light guide 72 having a ring-shaped cross-section is illustrated having a fiber 76, outer cladding 84 and inner cladding 86. In this embodiment, the hollow fiberoptic 72 acts as a sheath with a coherent fiber viewing bundle 88 disposed in the center of the cylindrical light guide fiber 76 in a manner so that the fiber 76 is an integral part of the viewing bundle 88. Such a structure is made possible by filling the preform of the hollow fiberoptic with multiple solid fiberoptics arranged in a coherent manner to form the viewing bundle 88. The resulting assembly is then drawn through an oven so as to meld the viewing bundle and the surrounding single fiber light guide cylinder 76 together to form a structure which contains a plastic coherent bundle surrounded by a plastic fiberoptic sheath. It is noted that in order for such a structure to be made, it is presently necessary for both the viewing bundle 88 and the core 76 as well as the outer cladding 84 and the inner cladding 86 to be made of plastic. Such a structure will have certain favorable characteristics and will be able to be manufactured at substantially lower costs than conventional systems.

Although the present single fiber light guide with a center region for receiving viewing bundles, transport channels, or other suitable devices therethrough has been disclosed with reference to the particular embodiments of the present invention, various modifications are possible without departing from the spirit and scope of the invention. It is therefore the object of the following claims to encompass all such modifications and variations that fall within the true spirit and scope of the invention.

What is claimed is:

1. A fiberoptic system comprising:
a hollow single optical fiber having a first end and a distal end, and outer cylindrical surface and an inner cylindrical surface each extending between the first end and the distal end, the region between the outer cylindrical surface and the inner cylindrical surface between the first end and the distal end defining an illuminating energy transport region for transporting illuminating energy from the first end to illuminate a region adjacent the distal end, the optical fiber having a center channel extending through the center of the optical fiber along the length thereof; and
function performing means comprising means extending through the center channel to the region adjacent the distal end for performing a predefined function adjacent the distal end.

2. The fiberoptic system of claim 1 further comprising inner cladding disposed on the inner cylindrical surface of the optical fiber.

3. The fiberoptic system of claim 1 further comprising outer cladding disposed on the outer cylindrical surface of the optical fiber.

4. The fiberoptic system of claims 1 or 3 further comprising an outer jacket disposed circumferentially around the optical fiber along its length.

5. The fiberoptic system of claim 3 further comprising inner cladding disposed on the inner cylindrical surface of the optical fiber.

6. The fiberoptic system of claim 5 wherein at least one of the optical fiber, the outer cladding and the inner cladding is optical grade plastic.

7. The fiberoptic system of claim 5 wherein at least one of the optical fiber, the outer cladding and the inner cladding is optical grade quartz.

8. The fiberoptic system of claim 5 wherein at least one of the optical fiber, the outer cladding and the inner cladding is optical grade glass.

9. The fiberoptic system of claims 1 or 5 wherein the function performing means comprises a coherent optical fiber viewing bundle slidably disposed along the center channel for viewing the region adjacent the distal end from the first end.

10. The fiberoptic system of claim 9 further comprising an outer jacket disposed circumferentially around the optical fiber along its length.

11. The fiberoptic system of claims 1 or 5 wherein the function performing means comprises a laser transport means slidably disposed along the center channel for transporting laser energy from the first end to the region adjacent the distal end.

12. A fiberoptic system having a light energy receiving end and a light energy delivery end for providing light energy adjacent the light energy delivery end, comprising:
a cylindrical, single fiber light guide having a center channel therethrough, the light energy being transported through the single fiber in the region around the center channel, the center channel providing physical access from the light receiving end to a region adjacent the light energy delivery end through the fiber; and
function performing means disposed along the center channel between the light energy receiving end and the light energy delivery end for performing a predefined function adjacent the light energy delivery end.

13. The fiberoptic system of claim 12 wherein the function performing means comprises a coherent optical fiber viewing bundle slidably disposed in the center channel.

14. The fiberoptic system of claim 12 wherein the single fiber has a ring-shaped cross-section with an outer cylindrical surface and an inner cylindrical surface, the fiberoptic system further comprising:
outer cladding disposed on the outer cylindrical surface of the fiber; and
inner cladding disposed on the inner cylindrical surface of the fiber.

15. The fiberoptic system of claims 12 or 14 wherein the function performing means disposed along the center channel comprises a laser transport means for communicating laser energy from the light energy receiving end to the light energy delivery end.

16. The fiberoptic system of claim 15 further comprising a laser energy generating means coupled to the laser transport means.

17. The fiberoptic system of claim 12 or 1 further comprising laser means for being selectively coupled to the fiber for generating laser energy and passing the energy into the fiber.

18. A fiberoptic system comprising:
a light guide comprising a single fiber having a first end and a distal end opposite the first end with a ring-shaped cross-section having an outer cylindrical surface and a central channel therethrough, the region between the outer cylindrical surface and the central channel defining an illuminating energy transport region for transporting illuminating energy along the light guide from the first end to the distal end; and
a laser transport means disposed in the central channel in integral relationship to the light guide for communicating laser energy from the first end to the distal end.

19. The fiberoptic system of claim 18 further comprising outer cladding disposed on the outer cylindrical surface of the single fiber.

20. The fiberoptic system of claim 19 further comprising inner cladding disposed on an inner cylindrical surface of the single fiber.

21. The fiberoptic system of claim 20 wherein at least one of the single fiber, outer cladding and inner cladding is an optical grade plastic.

22. The fiberoptic system of claim 20 wherein at least one of the single fiber, outer cladding and inner cladding is optical grade quartz.

23. The fiberoptic system of claim 20 wherein at least one of the single fiber, outer cladding and inner cladding is an optical grade glass.

24. The fiberoptic system of claim 18 further comprising inner cladding disposed on an inner cylindrical surface of the single fiber.

25. A fiberoptic system comprising a flexible wire for insertion into a biological subject to a position adjacent a predefined location inside a biological subject; and
a fiberoptic comprising a cylindrical, single fiber light guide having a hollow center channel therethrough, the wire slidingly located in the hollow center channel of the fiberoptic for enabling the fiberoptic to be slidingly advanced along the wire to the predefined location, illuminating energy being transported through the fiberoptic around the hollow center for illuminating the predefined location; and
function performing means comprising means extending through the center channel to the predefined location for performing a predefined function at the predefined location.

26. The fiberoptic system of claim 25 further comprising:
laser transport means slidingly disposed in the center channel for being positioned adjacent the predefined location; and
laser means for generating coherent electromagnetic energy and passing said energy into the laser transport means for supplying said energy at the predefined location.

27. The fiberoptic system of claim 25 further comprising laser means for being selectively coupled to the fiberoptic for generating laser energy and passing said laser energy into the fiberoptic and out from the fiberoptic adjacent the predefined location.

* * * * *

UNITED STATES PATENT AND TRADEMARK OFFICE
CERTIFICATE OF CORRECTION

PATENT NO.  : 4,768,858

DATED       : September 6, 1988

INVENTOR(S) : Hany M. G. Hussein

It is certified that error appears in the above-identified patent and that said Letters Patent is hereby corrected as shown below:

Col. 1, line 49, delete "be" and insert therefor --been--.

Col. 2, line 20, delete "Feb. 18" and insert therefor --Feb. 14--.

Col. 5, line 40, delete "ajdacent" and insert therefor --adjacent--.

Col. 5, line 54, delete "attentuation" and insert therefor --attenuation--.

Col. 6, line 48, before "outer" insert --an--.

Col. 8, line 7, after "therethrough" delete ",".

Signed and Sealed this

Thirteenth Day of June, 1989

Attest:

DONALD J. QUIGG

*Attesting Officer*    Commissioner of Patents and Trademarks